(12) United States Patent
Warburton-Pitt

(10) Patent No.: US 6,582,653 B1
(45) Date of Patent: Jun. 24, 2003

(54) APPARATUS AND METHOD FOR THE STERILIZATION-IN-PLACE OF INTRAVENOUS BAGS AND THE LIKE

(75) Inventor: Stephen Warburton-Pitt, Andover, NJ (US)

(73) Assignee: Saint-Gobain Performance Plastics Corporation, Wayne, NJ (US)

( * ) Notice: Subject to any disclaimer, the term of this patent is extended or adjusted under 35 U.S.C. 154(b) by 0 days.

(21) Appl. No.: 09/406,588

(22) Filed: Sep. 27, 1999

(51) Int. Cl.[7] .................................................. A61L 2/07
(52) U.S. Cl. ......................... 422/26; 422/25; 422/292; 422/297; 422/300; 422/302; 604/408
(58) Field of Search .......................... 422/25, 26, 292, 422/297, 300, 302; 604/408, 409, 410

(56) References Cited

U.S. PATENT DOCUMENTS

| 3,042,086 A | 7/1962 | Winchell | 141/390 |
|---|---|---|---|
| 3,722,557 A | 3/1973 | Huggins | |
| 4,657,540 A | 4/1987 | Iwamoto et al. | 604/408 |
| 4,727,705 A | * 3/1988 | Zahka | 53/425 |
| 4,906,103 A | 3/1990 | Kao | 366/130 |
| 5,789,684 A | 8/1998 | Masek et al. | 73/864.91 |

FOREIGN PATENT DOCUMENTS

CA          1137374          12/1982

* cited by examiner

*Primary Examiner*—Robert J. Warden, Sr.
*Assistant Examiner*—Sean E. Conley
(74) *Attorney, Agent, or Firm*—Selitto, Behr & Kim

(57) ABSTRACT

An apparatus and method for the sterilization-in-place of a bag assembly includes rigid bag and tube support members arranged in a clamshell configuration to surround and support the bag assembly so that pressurized steam can be supplied to the interior of the bag assembly without the danger of rupture.

4 Claims, 3 Drawing Sheets

APPARATUS AND METHOD FOR THE STERILIZATION-IN-PLACE OF INTRAVENOUS BAGS AND THE LIKE

BACKGROUND OF THE INVENTION

This invention relates to a bag assembly for use in pharmaceutical manufacturing and for holding health care related solutions and, more particularly, to an apparatus and a method for use in the sterilization-in-place of such a bag assembly.

Bag assemblies including a flexible bag and tubing connections are currently used in many applications, including intravenous delivery, blood transfusion and pharmaceutical manufacture. Before being filled, the bag assemblies must be sterilized. This is conventionally done initially at the place of manufacture before the bag assemblies are shipped, and the sterile bag assemblies are placed within individual packaging which protects their sterility. When a bag assembly reaches the location where it is to be filled, and the outer package is opened, unless this is done in a sterile environment, the bag assembly loses its sterility. Usually, clamps are applied to the tubes so that the interior of the bag remains sterile, but the interiors of the tubes distally of the clamps lose their sterility. This interior then has to be resterilized before the bag can be filled. It would be desirable to provide an apparatus and a method whereby the bag assembly does not have to be initially sterilized at the place of manufacture but instead the bag and tube interiors can be sterilized in place immediately before the bag is filled and at the same station where the bag is filled.

At the present time, virtually all such bag assemblies are manufactured of polyvinyl chloride (PVC). PVC is a commonly used inexpensive plastic material which is naturally hard. To soften such material so that it can be used as a flexible bag and as flexible tubing, plasticizers such as phthalate esters are added to the PVC to soften it. Recently there has been concern that phthalates may leach from the PVC to which they have been added, thereby contaminating aqueous fluids held in PVC bags and traveling through PVC tubing. Since PVC bags are used to store intravenous solutions and blood for transfusions, phthalates which leach from the PVC are infused directly into a patient's bloodstream. It has been proposed to provide a bag assembly manufactured entirely of silicone, which is phthalate-free and therefore obviates the above-discussed concerns. Such a bag assembly is formed of silicone tubing, with the bag being formed from large bore, thin walled silicone tubing and the inlet and outlet tubes being formed from small bore, thick walled silicone tubing. To sterilize such a bag assembly, it is known to use pressurized steam, which is an approved sterilization technique. However, the thin walled tubing making up the bag is limited insofar as the interior pressure it can tolerate. It would therefore be desirable to have apparatus which allows the interior of such a thin walled bag to be sterilized by pressurized steam while protecting the bag from excessive interior pressure which could rupture the bag.

SUMMARY OF THE INVENTION

According to the present invention, there is provided apparatus for use in performing sterilization-in-place of a silicone bag secured to a pair of tubes each communicating with the interior of the bag. The inventive apparatus comprises a plurality of rigid bag support members each including a respective cavity configured complemental to a respective portion of the exterior of the bag when the bag is inflated to a predetermined volume. The respective exterior portions together form the entire bag exterior with no overlap. The apparatus also includes at least one clamp coupled to the plurality of bag support members for holding together the plurality of bag support members so as to form a bag shell having an interior chamber equal in size and shape to the exterior of the bag when the bag is inflated to the predetermined volume.

In accordance with an aspect of the present invention, the apparatus further comprises a plurality of rigid tube support members each having a respective cavity configured complemental to a respective arcuate portion of the exterior circumference of a respective one of the tubes. The respective arcuate portions together form the entire respective tube exterior circumference with no overlap. At least one clamp is provided, which is adapted to hold together the plurality of tube support members so as to form a pair of tube shells each having an interior chamber equal in size and shape to a respective one of the tubes.

In accordance with another aspect of this invention, the plurality of bag support members consists of two rigid bag support members having substantially equal size cavities. The apparatus further comprises a hinge coupled to the two bag support members to allow pivoting movement about a pivot axis of one of the two bag support members relative to the other of the bag support members. The bag support member clamp has a first portion secured to one bag support member remote from the pivot axis and a second portion secured to the other bag support member remote from the pivot axis.

The inventive method for performing sterilization-in-place of a silicone bag secured to a pair of tubes each communicating with the interior of the bag comprises the steps of providing a plurality of rigid bag support members each including a respective cavity configured complemental to a respective portion of the exterior of the bag when the bag is inflated to a predetermined volume, wherein the respective exterior portions together form the entire bag exterior with no overlap, and placing the bag on at least one of the bag support members. Further steps include clamping the plurality of bag support members so as to form a bag shell having an interior chamber equal in size and shape to the exterior of the bag when the bag is inflated to the predetermined volume, and then applying pressurized steam to one of the tubes.

BRIEF DESCRIPTION OF THE DRAWINGS

The foregoing will be more readily apparent upon reading the following description in conjunction with the drawings in which like elements in different figures thereof are identified by the same reference numeral and wherein.

DETAILED DESCRIPTION

Figure 1:
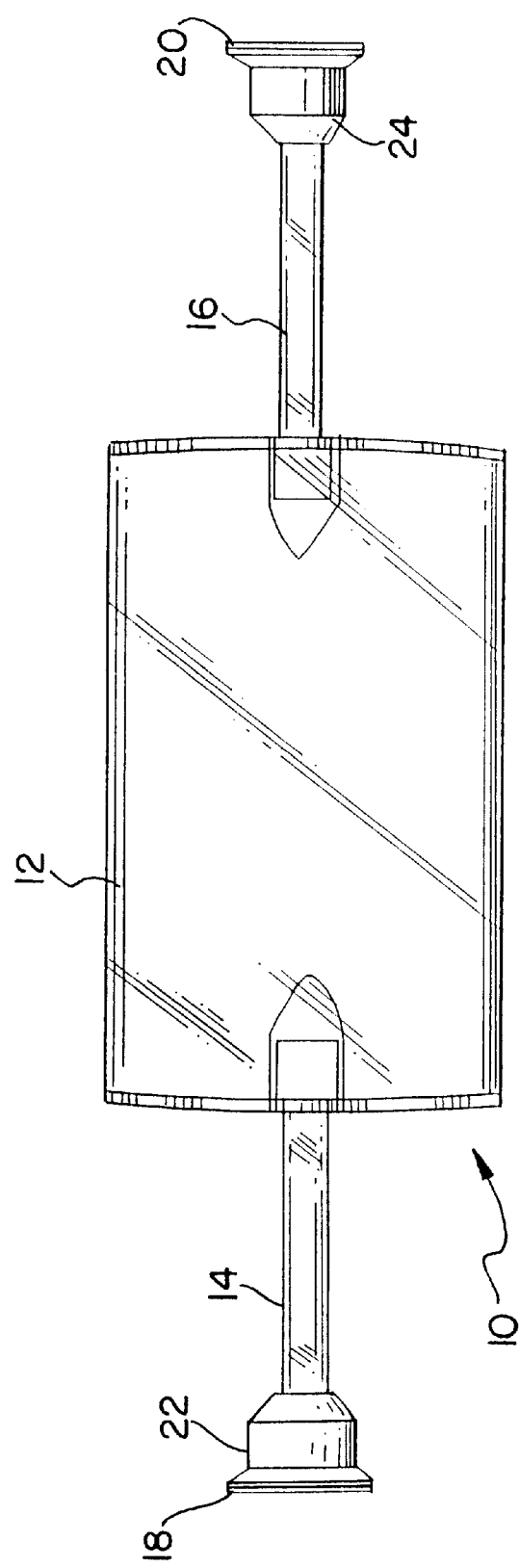
FIG. 1 is a plan view of a bag assembly of the type which can be sterilized using the apparatus and method of the present invention.

FIG. 1 shows a bag assembly, designated generally by the reference numeral 10, with which the present invention may be practiced. The bag assembly 10 is preferably formed of silicone and is formed from large bore, thin walled silicone tubing making up the bag 12 and small bore, thick walled silicone tubing making up the inlet and outlet tubes 14, 16. Each of the tubes 14, 16 extends into a respective one of the opposed ends of the bag 12 so that the central bores of the tubes 14, 16 are in communication with the interior of the bag 12. Preferably, the tubes 14, 16 are arranged substantially coaxially and each of the ends of the bag 12 is flattened and sealed to itself and to a respective one of the tubes 14, 16 as by adhesive or the like. The tubes 14, 16 are terminated by flanges 18, 20, respectively, and stainless steel backup cups 22, 24 are slidably mounted on the tubes 14, 16, respectively, to provide support for the flanges 18, 20 and allow the tubes 14, 16 to be connected to similar couplings.

Figure 2:
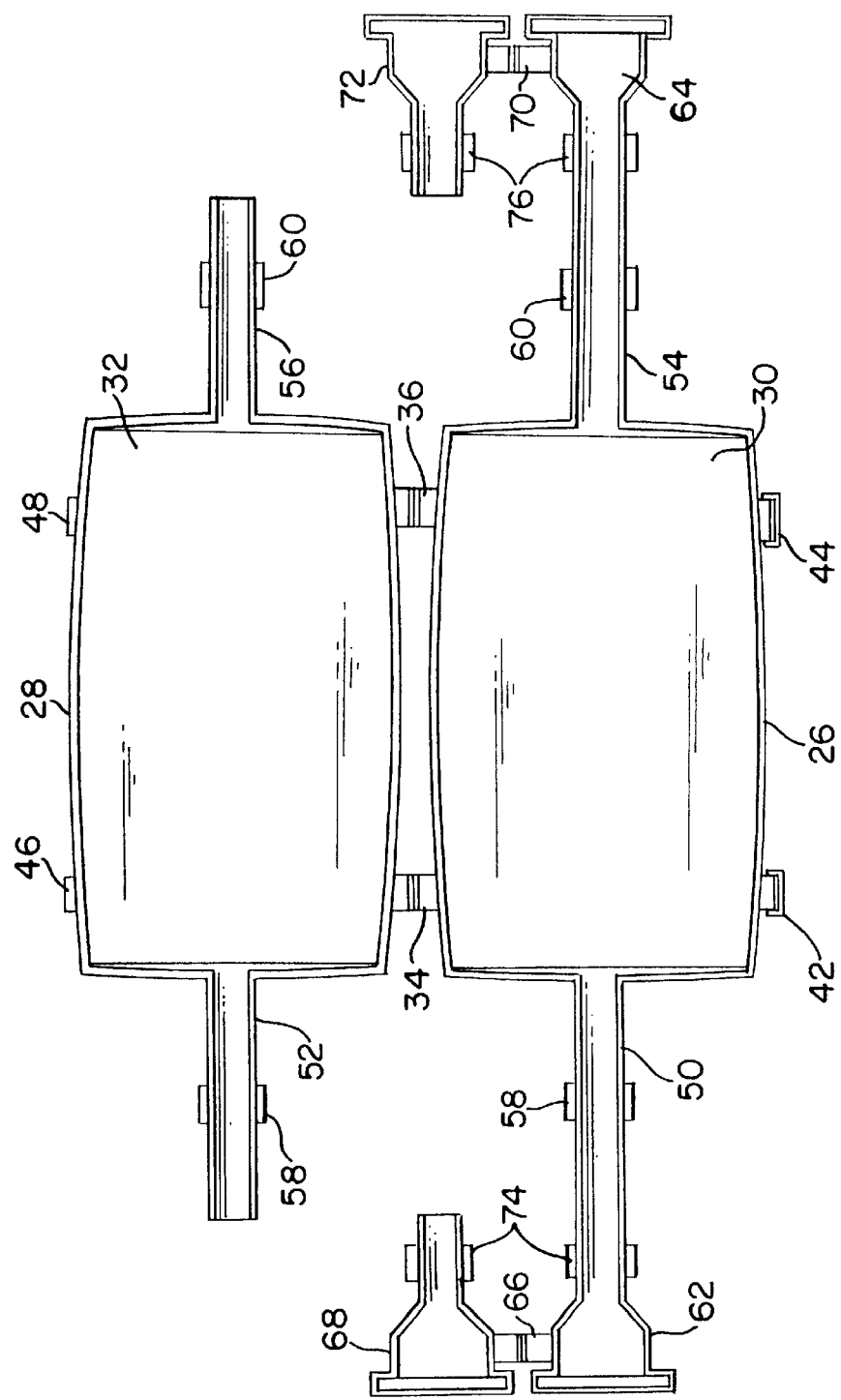
FIG. 2 is a plan view of an embodiment of apparatus constructed in accordance with the present invention.
Figure 3:
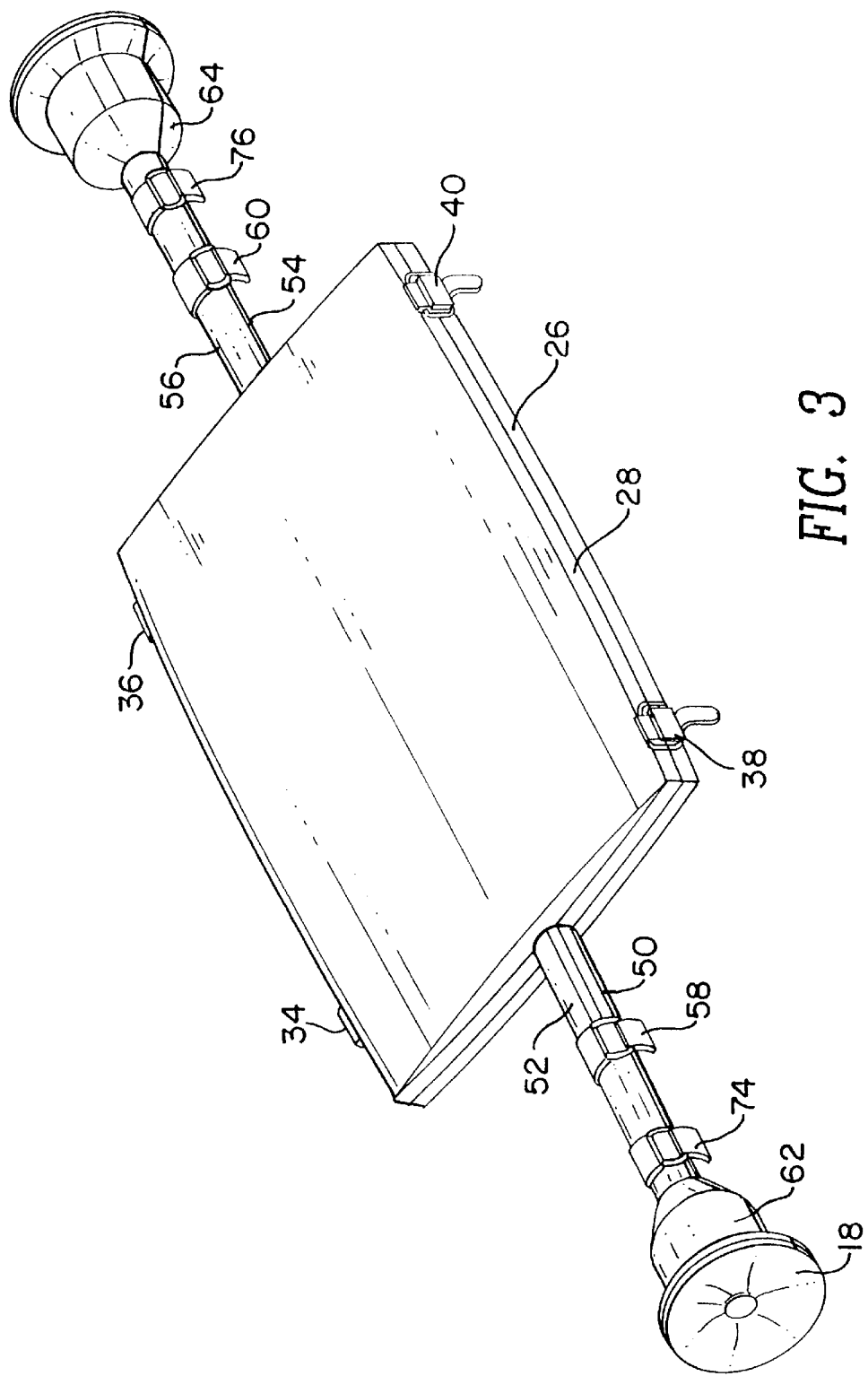
FIG. 3 is a perspective view of the apparatus shown in FIG. 2 holding the bag assembly shown in FIG. 1.

Since the bag 12 is preferably made from thin walled silicone tubing, it is limited in the interior pressure which it can tolerate without rupturing. Therefore, using pressurized steam to sterilize the bag assembly 10 is potentially damaging to the bag 12. In order to overcome this limitation and allow for sterilization-in-place of the bag assembly 10, the apparatus shown in FIGS. 2 and 3 is provided. This apparatus includes a pair of rigid bag support members 26, 28. Each of the bag support members 26, 28 is preferably made of a rigid material such as stainless steel and includes a respective cavity 30, 32 which is configured complemental to a respective portion of the exterior of the bag 12 when the bag 12 is inflated to a predetermined limiting volume. The respective exterior portions together form the entire bag exterior with no overlap. Preferably, there are two such bag support members 26, 28, each of which has its respective cavity 30, 32 configured complemental to one half of the exterior of the bag 12. The bag support members 26, 28 are coupled together by hinges 34, 36 to allow pivoting movement about a pivot axis of one of the bag support members 26, 28 relative to the other of the bag support members 28, 26. Thus, the two bag support members 26, 28, together with the hinges 34, 36, form a "clamshell" for holding the bag 12 therein.

Clamps 38, 40 are provided along the edges of the bag support members 26, 28 remote from the hinges 34, 36. Each of the clamps 38, 40 has a respective first portion 42, 44 secured to the bag support member 28 and a respective second portion 46, 48 secured to the bag support member 28. When the bag support members 26, 28 are pivoted toward each other and locked together by the clamps 38, 40, they form a bag shell having an interior chamber equal in size and shape to the exterior of the bag 12 when the bag 12 is inflated to the predetermined limiting volume. Thus, pressurized steam can be applied to the interior of the bag 12 when the bag 12 is held within the clamped bag support members 26, 28 because expansion of the bag 12 is limited to the predetermined volume defined by the bag shell, thereby preventing overexpansion and rupturing of the bag 12.

While the tubes 14, 16 have been described as being made of thick walled silicone tubing, it may be desired for the sake of economy to use thin walled tubing for the tubes 14, 16. Accordingly, the apparatus shown in FIGS. 2 and 3 may be provided with tube support members 50, 52, 54, 56 formed integrally with and of the same material as the bag support members 26, 28. Thus, each of the tube support members 50, 52, 54, 56 is a semicylindrical piece sized so that when a pair of the tube support members are placed together, they form a cylindrical cavity having an interior circumference equal to the exterior circumference of the tubes 14, 16. Clamp 58 holds the tube support members 50, 52 together and clamp 60 holds the tube support members 54, 56 together. The edges of the bag support member 26 and the tube support members 50, 54 lie in a first plane, and the edges of the bag support member 28 and the tube support members 52, 56 lie in a second plane, so that when the bag support member 28, along with the tube support members 52, 56, is pivoted about the pivot axis defined by the hinges 34, 36, the first and second planes become coextensive.

To accommodate the flanges 18, 20 and the backup cups 22, 24, at its distal end the tube support member 50 is formed with an enlarged portion 62 configured complemental to one half of the backup cup 22 and the flange 18. Similarly, the tube support member 54 is formed at its distal end with an enlarged portion 64 configured complemental to one half of the backup cup 24 and the flange 20. Secured to the enlarged portion 64 by the hinge 66 is a support member 68 configured complemental to the other half of the backup cup 62 and the flange 18 and to the other half of the distal end of the tube 14. Similarly, secured to the enlarged portion 64 by the hinge 70 is a support member 72 configured complemental to the other half of the backup cup 24 and the flange 20 and to the other half of the distal end of the tube 16. The support member 68 is held tightly to the enlarged portion 64 by the clamp 74 and the support member 72 is held tightly to the enlarged portion 64 by the clamp 76.

To perform sterilization-in-place of the bag assembly 10 with the apparatus shown in FIGS. 2 and 3, the unsterilized bag 12 is placed in the cavity 30 of the bag support member 26 and the tubes 14, 16 are placed in the interiors of the tube support members 50, 54, respectively, with the backup cup 22 and the flange 18 being placed in the enlarged portion 62 and the backup cup 24 and the flange 20 being placed in the enlarged portion 64. The bag support member 28, along with the tube support members 52, 56, is then pivoted about the hinges 34, 36 and the clamps 38, 40, 58, 60 are secured. The support members 68, 72 are then pivoted about the hinges 66, 70, respectively, and the clamps 74, 76 are secured. The assembly is then transported to a sterilization station, which preferably is part of a bag filling station. One of the flanges 18, 20 is then connected to the sterilization station and pressurized steam is provided. The pressurized steam travels through one of the tubes 14, 16, through the bag 12, and through the other of the tubes 16, 14. This process sterilizes the interior of the bag 12 and the tubes 14, 16. The steaming is terminated and material from the filling station is then supplied to fill the bag 12. The clamps 74, 76 may then be released and the ends of the tubes 14, 16 are clamped to seal the contents of the bag 12. The clamps 42, 46, 58, 60 may then be released and the filled bag is removed from the support apparatus.

Accordingly, there has been disclosed an improved sterilization-in-place apparatus and method for a bag assembly. While an illustrative embodiment of the present invention has been disclosed herein, it is understood that various modifications and adaptations to the disclosed embodiment are possible and it is intended that this invention be limited only by the scope of the appended claims.

What is claimed is:

1. Apparatus for use in performing sterilization-in-place of a silicone bag secured to a pair of tubes each communicating with the interior of the bag, comprising:

a plurality of rigid bag support members each including a respective cavity configured complemental to a respective portion of the exterior of the bag when the bag is inflated to a predetermined volume, wherein the respective exterior portions together form the entire bag exterior with no overlap;

at least one clamp coupled to the plurality of bag support members for holding together the plurality of bag support members so as to form a bag shell having an interior chamber equal in size and shape to the exterior of the bag when the bag is inflated to the predetermined volume;

a plurality of rigid tube support members each having a respective cavity configured complemental to a respective arcuate portion of the exterior circumference of a respective one of said tubes, wherein the respective arcuate portions together form the entire respective tube exterior circumference with no overlap; and at least one clamp adapted to hold together the plurality of tube support members so as to form a pair of tube shells each having an interior chamber equal in size and shape to a respective one of said tubes.

2. Apparatus for use in performing sterilization-in-place of a silicone bag secured to a pair of tubes each communicating with the interior of the bag, comprising:

two rigid bag support members each including a respective cavity configured complemental to a respective portion of the exterior of the bag when the bag is inflated to a predetermined volume, wherein the cavities are of substantially equal size and the respective exterior portions together form the entire bag exterior with no overlap;

at least one clamp coupled to the two bag support members for holding together the two bag support members so as to form a bag shell having an interior chamber equal in size and shape to the exterior of the bag when the bag is inflated to the predetermined volume;

a hinge coupled to said two bag support members to allow pivoting movement about a pivot axis of one of said bag support members relative to the other of said bag support members;

wherein said at least one clamp has a first portion secured to said one bag support member remote from said pivot axis and a second portion secured to said other bag support member remote from said pivot axis;

a respective pair of semicylindrical rigid tube support members for each of said tubes, each of said tube support members being secured to a respective one of said two bag support members; and at least one clamp coupled to each respective pair of said tube support members for holding together the respective pair of tube support members so as to form a pair of tube shells each capable of accommodating therein a respective one of said tubes.

3. A method for use in performing sterilization-in-place of a silicone bag secured to a pair of tubes each communicating with the interior of the bag, comprising the steps of:

providing a plurality of rigid bag support members each including a respective cavity configured complemental to a respective portion of the exterior of the bag when the bag is inflated to a predetermined volume, wherein the respective exterior portions together form the entire bag exterior with no overlap;

placing the bag on at least one of the bag support members;

clamping the plurality of bag support members together around the bag so as to form a bag shell having an interior chamber equal in size and shape to the exterior of the bag when the bag is inflated to the predetermined volume; and applying pressurized steam to the interior of at least one of the tubes.

4. The method according to claim 3 further comprising the steps of:

providing a plurality of rigid tube support members each having a respective cavity configured complemental to a respective arcuate portion of the exterior circumference of a respective one of said tubes, wherein the respective arcuate portions together form the entire respective tube exterior circumference with no overlap;

placing each tube on a respective tube support member; and clamping together the plurality of tube support members so as to form a pair of tube shells each surrounding a respective tube and each having an interior chamber equal in size and shape to the respective tube.

* * * * *